United States Patent
Diamond

(10) Patent No.: US 10,761,024 B2
(45) Date of Patent: Sep. 1, 2020

(54) APPARATUS AND METHOD FOR EXTRACTING LOW INTENSITY PHOTONIC SIGNALS

(71) Applicant: INSPECTION TECHNOLOGIES LIMITED, Warwickshire (GB)

(72) Inventor: Geoffrey Graham Diamond, Warwickshire (GB)

(73) Assignee: INSPECTION TECHNOLOGIES, LTD (GB)

(*) Notice: Subject to any disclaimer, the term of this patent is extended or adjusted under 35 U.S.C. 154(b) by 0 days.

(21) Appl. No.: 16/312,741

(22) PCT Filed: Jun. 23, 2017

(86) PCT No.: PCT/GB2017/051844
§ 371 (c)(1),
(2) Date: Dec. 21, 2018

(87) PCT Pub. No.: WO2017/221024
PCT Pub. Date: Dec. 28, 2017

(65) Prior Publication Data
US 2019/0219507 A1    Jul. 18, 2019

(30) Foreign Application Priority Data

Jun. 23, 2016 (GB) .................... 1610988.6

(51) Int. Cl.
*G06T 5/50* (2006.01)
*G01N 21/64* (2006.01)
(Continued)

(52) U.S. Cl.
CPC ......... *G01N 21/6408* (2013.01); *G01N 21/63* (2013.01); *G01N 21/6456* (2013.01);
(Continued)

(58) Field of Classification Search
CPC . G06T 2207/30242; G06T 5/50; G01N 21/63; G01N 21/6408; G01N 21/6454
See application file for complete search history.

(56) References Cited

U.S. PATENT DOCUMENTS

| | | | |
|---|---|---|---|
| 6,026,319 A | 2/2000 | Hayashi | |
| 2006/0004292 A1 | 1/2006 | Beylin | |
| 2008/0225141 A1* | 9/2008 | Ogawa | H04N 5/3572 348/251 |

FOREIGN PATENT DOCUMENTS

| | | | |
|---|---|---|---|
| EP | 1 035 409 A2 | 9/2000 | |
| EP | 2 975 381 A1 | 1/2016 | |
| EP | 2 980 562 A1 | 3/2016 | |

OTHER PUBLICATIONS

International Search Report for corresponding PCT Application No. PCT/GB2017/051844 dated Aug. 31, 2017.

* cited by examiner

Primary Examiner — David P Porta
Assistant Examiner — Fani Boosalis
(74) Attorney, Agent, or Firm — Daniel S. Polley, P.A.

(57) ABSTRACT

A system for detecting stimulated emission from a material of interest comprising: an excitation source; and an imaging component; wherein, in use, the system is configured to: a) emit excitation radiation from the excitation source for a first time period, the excitation radiation having a wavelength suitable for inducing stimulated emission in the material of interest; b) capture a first image via the imaging component, the first image substantially consisting of a background illumination component and a stimulated emission component; c) stop emitting excitation radiation for a second time period; d) capture a second image via the imaging component, the second image substantially consisting of the background illumination component; e) create a difference image (Continued)

corresponding to the difference between the first and second images, such that the difference image includes any stimulated emission signals from the material of interest.

16 Claims, 7 Drawing Sheets

(51) Int. Cl.
*G06T 7/00* (2017.01)
*G06T 7/246* (2017.01)
*G01N 21/91* (2006.01)
*G16H 30/20* (2018.01)
*G01N 21/63* (2006.01)

(52) U.S. Cl.
CPC ............... *G01N 21/91* (2013.01); *G06T 5/50* (2013.01); *G06T 7/0016* (2013.01); *G06T 7/248* (2017.01); *G16H 30/20* (2018.01); *G01N 2021/646* (2013.01); *G01N 2201/0221* (2013.01); *G06T 2207/10064* (2013.01); *G06T 2207/30004* (2013.01); *G06T 2207/30108* (2013.01)

APPARATUS AND METHOD FOR EXTRACTING LOW INTENSITY PHOTONIC SIGNALS

This application claims the benefit of and priority to PCT Application No. PCT/GB2017/051844, filed 23 Jun. 2017 and Great Britain (GB) Application No. 1610988.6, filed 23 Jun. 2016. Both applications are incorporated by reference in their entireties for all purposes. This application is also the U.S. National Stage application entry under 35 U.S.C. § 371 from PCT Application No. PCT/GB2017/051844.

FIELD OF INVENTION

The present invention relates to the detection of photonic signals, in particular to detecting fluorescence signals from a sample in particular for use in non-destructive testing, or medical imaging.

BACKGROUND

The detection of fluorescence signals is currently employed for a variety of different purposes.

For example, fluorescence techniques are used in the field of non-destructive testing (NDT). Such techniques can be applied to detection of small discontinuities such as inclusions, seams, shrink cracks, tears, laps, flakes, welding defects, grinding cracks, quenching cracks and fatigue cracks. In such techniques, a fluorescent material is applied to an item of interest in such a way that it preferentially accumulates in cracks, surface flaws and other defects on the item of interest. The item is then illuminated with electromagnetic radiation having a suitable wavelength so as to excite the material and cause the fluorescent material to fluoresce—this provides a user with a visual indication of the cracks/surface flaws/other defects on the item. Such defects might otherwise be difficult or even impossible to detect during a simple visual inspection of the item. Exemplarily known techniques employing this principle include Fluorescent Magnetic Particle Inspection (FMPI) and Penetrant Inspection for surface cracks and surface flaws in non-ferromagnetic and both surface and sub-surface cracks and flaws in ferromagnetic materials respectively. NDT inspection of articles via the detection of fluorescence in the above manner is of great importance across many industrial sectors and is used for example in forgings, foundry, fabrication, atomic energy, aerospace, ship building, railways, and automotive, applications. It is an inspection method which is prescribed by various standards bodies (for example, British Standards BS4489 and BS667, Civil Aviation Authority Air Worthiness Notice 95 and Rolls Royce Standard RPS702).

Other examples applications are for inspection of product within the electronics and semiconductor industries where a common use of penetrant fluorescent dyes is within pressured vessels, pressurised to approximately 7 bar, which contain signal diodes. Under these high pressures, fluorescent penetrant dye is forced into cracks which occur typically at the metal electrode to glass junction interface. Currently, manual inspection and detection of defective components exposed to penetrant dye under pressure is performed in very low light conditions.

As another example, fluorescence techniques are also used in medical contexts, in applications in fields such as Fluorescence Image Guided Surgery (FIGS) and Enzyme Linked Immunosorbent Assay (ELISA) techniques. The former is a surgical technique which detects fluorescently labelled structures such as cancers and tumours during surgery. The latter is a commonly used analytic biochemistry assay technique used in medicine, plant pathology and also as a quality control measure in various industries that produces fluorescence to detect the presence of a substance, usually an antigen or other substance. The techniques has further applications, for example in detecting auto-fluorescing biofilms and other pathogens, cell counting, microscopy and identification of chemical species.

However, in the known fluorescence techniques discussed above, the amount of fluorescence produced is typically low. This leads to poor signal to noise ratios when the technique is used in the presence of background illumination and makes it difficult for cameras and the human eye (for example that of the person conducting the test) to discern the fluorescence signal over the background illumination. For example, in NDT techniques such as FMPI and Penetrant Inspection, an inspector may be unable to see fluorescence associated with a surface defect when viewing an item in ambient daylight. In the case of FIGS, the low levels of fluorescence often requires the operating theatre lights to be dimmed or even switched off. In the case of ELISA, poor signal to noise ratios can limit the environments in which it can be deployed and the accuracy of quantitative analyses.

It is known in the art to improve signal to noise ratios of such fluorescence techniques by minimising the level of background illumination. For example, in surgical techniques, the ambient lighting is reduced to a level suitable for detecting fluorescence as noted above. However, such reductions in ambient lighting may be inappropriate, since higher lighting levels may be required for normal surgical purposes. For NDT applications ambient lighting must be low enough to comply with relevant requirements, (as specified in ASTM E709, for example) which often limits its deployment to being used indoors or under specially constructed covered awnings and tents whilst working outdoors in daylight conditions (direct sunlight). Limiting the use of NDT fluorescence techniques to indoor environments or requiring the installation of purpose-built tents or other structures requires additional time and manpower to perform the testing, thereby increasing costs and the time associated with performing such tests.

In many NDT applications, the sample of interest may be moving during testing. For example, in the case of the inspection of objects such as castings and forged parts, the objects can be on a fast-moving conveyor belt. Similarly, the apparatus used for testing may itself be moving (for example, if the apparatus is being hand-held). This poses a problem for conventional machine-vision camera systems for detecting fluorescence, in that they are often unable to capture clear images of the object of interest because there is an inherent delay between the capture of successive images. It is therefore possible for a defect to go undetected, either because the resulting image is too unclear to recognise the defect, or because the area of the object comprising the defect passed the field of view of the conventional machine-vision camera during the system's "dead time" between captured image frames. Conventional machine vision cameras are known to have different frame rates. However even with the faster available frame rates, such systems typically include a substantial "dead time" between captured image frames. Accordingly, such systems do not solve the problem above in relation to moving images.

Accordingly, there is a need to provide a more effective means to improve the signal to noise ratio of such fluorescence techniques in situations where background illumination is present. In addition, there is a need to provide such a means that is also capable of accurately detecting fluorescence in moving objects.

SUMMARY OF INVENTION

In order to mitigate at least some of the issues above, the present invention provides a system and method as defined in the appended claims.

The present invention provides a system for detecting stimulated emission from a material of interest comprising: an excitation source; and an imaging component; wherein, in use, the system is configured to: a) emit excitation radiation from the excitation source for a first time period, the excitation radiation having a wavelength suitable for inducing stimulated emission in the material of interest; b) capture a first image via the imaging component, the first image substantially consisting of a background illumination component and a stimulated emission component; c) stop emitting excitation radiation for a second time period; d) capture a second image via the imaging component, the second image substantially consisting of the background illumination component; e) create a difference image corresponding to the difference between the first and second images, such that the difference image includes any stimulated emission signals from the material of interest.

Advantageously the above system allows for effective detection of stimulated emission (for example fluorescence) even in the presence of high levels of background illumination. Thus, the present invention avoids the need for items to be moved indoors or covered with tents or awnings when performing non-destructive testing techniques such as FMPI, and avoids the need for dimly-lit environments when performing medical techniques such as FIGS or ELISA. Indeed, embodiments of the present invention have detected fluorescent radiation of 200 lux or lower, in the presence of background illumination of over 100,000 lux.

Moreover, the present invention allows images to be obtained in real-time, giving a user real-time indications of the presence of a material of interest (for example a fluorescent material).

In a preferred embodiment, the system comprises two imaging components (and optionally more than two imaging components) and is configured to cause each of the imaging components to capture an image in a temporal sequence. Preferably the system cycles through each imaging component to capture the successive first and second images. For example, a first imaging component captures the first image in step (b) and a second imaging component captures the second image in step (d). Advantageously this allows the frame rate of image capture be increased far beyond the frame rate of a single camera system, thereby enabling rapid, accurate detection of defects, particularly useful when analysing moving objects.

Preferably the system also performs automatic image analysis on the difference images to automatically identify features corresponding to fluorescence from the fluorescent material.

The system can advantageously be embodied in a stationary system suitable for scanning large areas of an object. Alternatively, the system can be embodied in a handheld device, preferably also comprising a display, thereby providing a portable and convenient tool for detecting stimulated emission (such as fluorescence) in environments with high background illumination levels.

According to further aspects of the invention there is also provided a method for detecting stimulated emission from a fluorescent material of interest comprising: a) illuminating a sample with excitation radiation for a first time period, the excitation radiation having a wavelength suitable for inducing stimulated emission fluorescence in the fluorescent material of interest; b) capturing a first image of the sample during the first time period; c) stop illuminating the sample with excitation radiation for a second time period; d) capturing a second image of the sample during the second time period; e) creating a difference image corresponding to the difference between the first and second images, such that the difference image includes any stimulated emission fluorescence signals from the material of interest.

In a preferred embodiment, the method comprises capturing the images using two imaging components (and optionally more than two imaging components) in a temporal sequence. Preferably the method includes cycling through each imaging component when capturing the successive first and second images. For example, step (b) is performed using a first imaging component step (d) is performed by a second imaging component. Advantageously this allows the frame rate of image capture be increased far beyond the frame rate of a single camera system, thereby enabling accurate detection of defects in moving objects.

BRIEF DESCRIPTION OF THE DRAWINGS

Aspects of the invention are further described below with reference to the following drawings, by way of example only.

DETAILED DESCRIPTION

The embodiments below are discussed in relation to the accompanying drawings, in which like numerals refer to like elements.

The embodiments below will be described generally from the point of view of non-destructive testing, in which a fluorescent material is applied to a sample for the purposes of detecting cracks, surface flaws and other defects. However, it will be appreciated that the disclosed embodiments are also suitable for use in other situations in which fluorescent materials are excited and it is desired to view the resulting fluorescence, such as when performing the FIGS or ELISA techniques discussed above.

Figure 1:
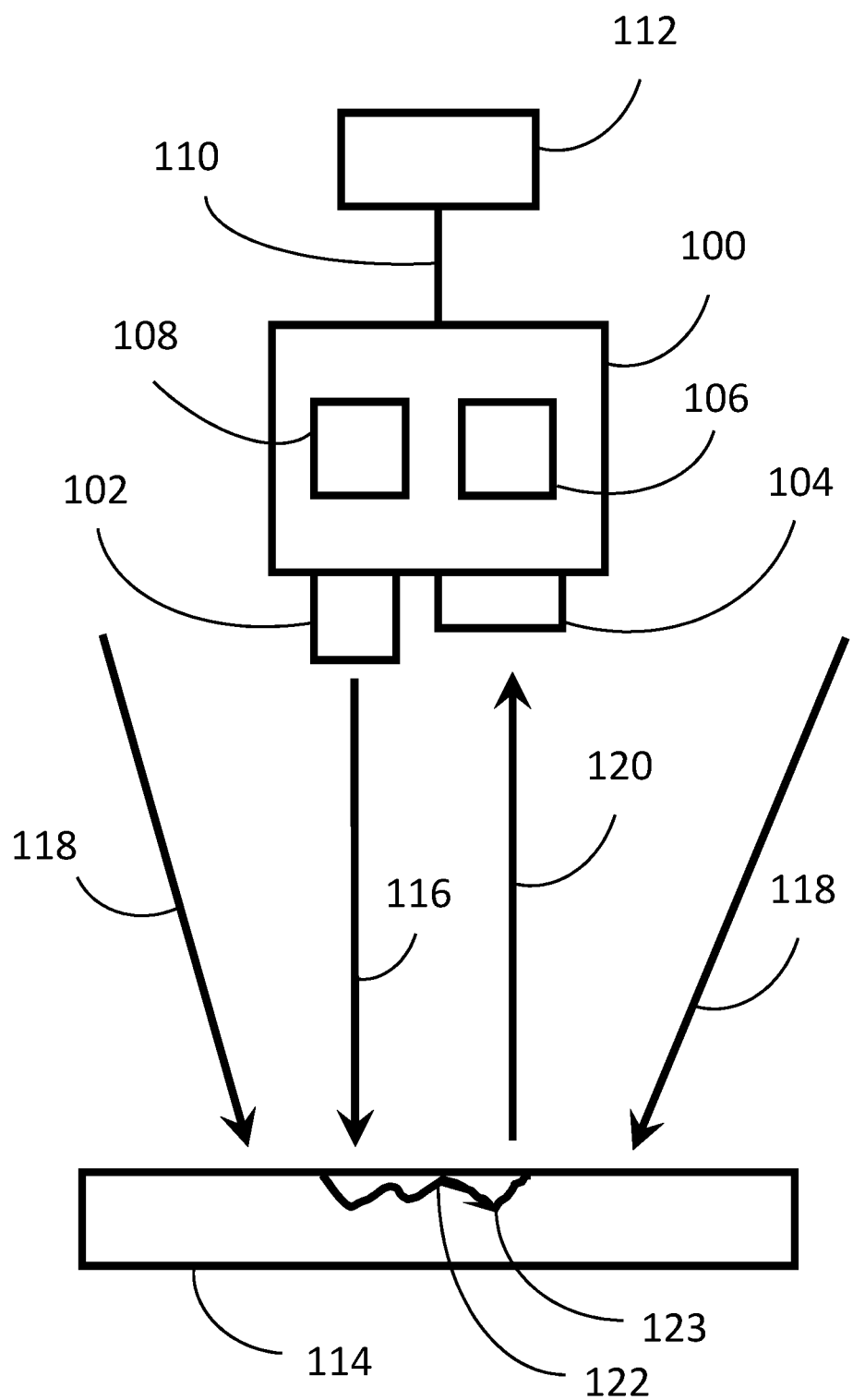
FIG. 1 shows a schematic of a device for detecting fluorescence signals in accordance with an aspect of the present invention.

FIG. 1 shows a schematic of a device for detecting fluorescence signals 100. The device 100 comprises an excitation source 102 and an imaging component 104, image processing circuitry 106 and synchronisation circuitry 108. In a preferred embodiment, the device comprises at least two imaging components, as discussed in more detail below with respect to FIGS. 5A to 5C. FIG. 1 also shows a sample 114 comprising a surface defect 122, which has had fluorescent material 123 applied to it such that fluorescent material 123 is predominantly present in the surface defect 122.

The excitation source 102 is configured to provide electromagnetic radiation 116 having a wavelength suitable for inducing fluorescence in the fluorescent material 123. In an embodiment, the excitation source 102 is an ultraviolet (UV) radiation source, in further embodiments it is a source of another wavelength range which is able to excite a fluorescent material to enable the source to fluoresce. The wavelength of excitation radiation 116 and thus the excitation source is chosen based on the fluorescent material of interest. For example, when the fluorescent material of interest 123 is a powder such as the commercially available Magnaflux™ 14-HF (or similar) such Magnaflux™ ZL-60C as for use in Fluorescent Magnetic Particle Inspection (FMPI). A suitable range of wavelengths for excitation radiation 116 for such materials is between 350 nm to 450 nm. For other fluorescent materials, the range of possible excitation wavelengths range between 200 nm to 2000 nm depending on the material.

On absorbing the excitation radiation 116, the fluorescent material 123 emits radiation 120 due to fluorescence. The emitted radiation 120 is then detected by the imaging component 104. The imaging component is preferably a digital imaging device, such as a digital camera, and preferably includes optical elements configured to form an image of the sample 114, which can be captured by the imaging component.

In preferred embodiments, the imaging component 104 comprises one or more background filters. Such background filters are preferably optical band-pass filters, configured to allow wavelengths corresponding to the fluorescence of interest to reach the imaging component 104, whist substantially preventing a range of other wavelengths from reaching the imaging component 104. Advantageously the filters reduce the levels of background noise in images obtained by the imaging component and reduce the need for noise reduction processing to be applied to the images (in turn, resulting in a faster fluorescence detection process). In addition, this helps to compensate for any background illumination intensity variations between successive images (which improves the accuracy of the image subtraction technique discussed below). For example, in the case that the fluorescent material 123 is a fluorescent magnetic dye such as Magnaflux™ 14-HF (or similar) and the excitation source is a UV source, a suitable choice of background filter is a green band-pass filter that allows transmission of wavelengths between 485 and 565 nm (which is a peak emission wavelength of the penetrant dye). For other fluorescent materials with different emission wavelengths, which may lie between 200 nm to 2000 nm, other appropriate band-pass filters are employed.

Optionally, there is also be provided a computer system 112 connected to the device 100 via a data connection 110 (either a wired or wireless connection). The optional computer system 112 is preferably used to display images showing the fluorescence of the fluorescent material 123.

Whilst the above embodiments discussed providing the imaging component 104, the excitation source 102 and circuitry 106, 108 in a single device 100, in other embodiments such components are provided separately. For example, in some embodiments there is provided a system for detecting fluorescence signals, comprising an excitation source 102 and an imaging component 104 as separate units.

In such embodiments, optionally, rather than providing synchronisation circuitry 108 and image processing circuitry 106 at either unit, control of the imaging component 104 and the excitation source 102, and image processing tasks is instead performed at an external computing device 112.

Advantageously, the device 100 can be operated in the presence of background illumination 118. Moreover, the device 100 can provide a high signal to noise ratio image of the fluorescent material 123 (and hence, in this case, the surface defect 122) when high levels of background illumination 118 are present, via the control of the imaging component 104 and the excitation source 102 via the synchronisation circuitry 108. In particular, the synchronisation circuitry 108 synchronises the operation of the imaging component 104 and the excitation source 102, such that the imaging component 104 captures a first image of the sample 114 during or shortly after illumination of the sample by the excitation source 102 (such that the first image comprises components due to background radiation 118 reflected by the sample 114 onto the imaging component and emitted radiation 120 caused by excitation of the fluorescent material), and a second image captures when the sample 114 is not being illuminated by the excitation source 102 (such that the second image substantially comprises components due to background radiation 118 reflected by the sample 114 only, with little or no components due to fluorescence of the fluorescent material 123). The operation of the synchronisation circuitry 108 therefore performs "lock-in" operation of the imaging component 104 and the excitation source 102. The two images can then be subtracted to obtain a difference image showing any fluorescence in a clear manner. This "lock-in" operation and associated image subtraction is described in further detail below in relation to FIG. 2.

Figure 2:
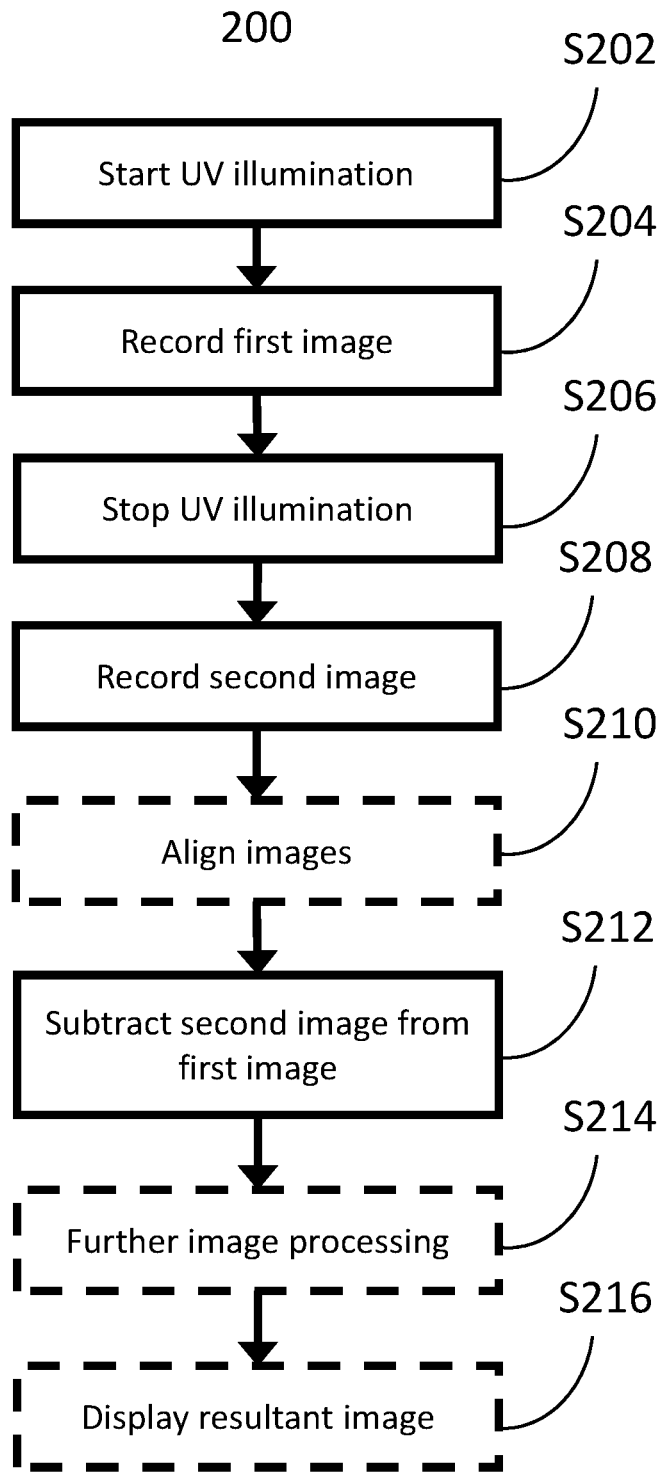
FIG. 2 shows a method for detecting fluorescence signals in accordance with an aspect of the present invention.

FIG. 2 shows a method 200 for detecting fluorescence signals. The method 200 can be used with the device 100 (or the system) as described above. The device 100 is positioned for imaging an object to which a fluorescent material 123 has been applied, such as sample 114.

At step S202 the device 100 is configured to start producing excitation radiation 116 (for example UV illumination). Subsequently at step S204, the imaging component 104 is configured to capture a first image of the sample. In embodiments comprising two or more imaging components, preferably a first imaging component captures the first image in step S204. The first image will contain components due to the emitted radiation 120 from the fluorescent material 123 and reflected light due to the background illumination 118.

In some circumstances, a portion of the excitation radiation 116 may undesirably be reflected by the sample 116 (or other object) towards the imaging component rather than inducing fluorescence in the fluorescent material 123. Preferably the device 100 is configured to prevent components due to such reflected light from the excitation radiation 116 being included in the first image. Advantageously this makes the image subtraction process and any subsequent image processing as described below more accurate and less computationally complex. To achieve this, preferably the device 100 further comprises one or more optical filters configured to prevent wavelengths of radiation corresponding to the wavelength of the excitation radiation from reaching the imaging component 104. For example, in the case of the excitation radiation being UV radiation, a UV filter is preferably provided. Such a filter preferably forms part of the imaging component 104 itself (for example a band pass filter included in a digital camera). For some wavelengths of excitation radiation, optical components such as lenses included in the imaging component have sufficient reflection and absorption properties to filter out the excitation wavelengths before they can reach a sensor at the imaging component.

As an alternative to using filters as described above, the first image can be taken a short time after the excitation source 102 stops producing excitation radiation, before the fluorescent material 123 has stopped fluorescing. Whilst this requires fewer physical components, the amount of emitted radiation 120 detected is less.

It will be appreciated that in some situations, the amount of excitation radiation 116 being reflected by the sample 114 towards the imaging component 104 is significantly less than the emitted radiation 120. This is the case for example if the excitation radiation 116 was incident on the sample 116 within a certain angle or range of angles relative to the optical axis of the imaging component. In such situations, there is no need for provisions to remove reflected excitation radiation 116 from the first image, since it does not affect the image subtraction and processing described below.

In step S206 the illumination by the excitation source 102 is stopped, such that the sample 114 is only being illuminated by ambient background radiation 118. Whilst there is no excitation radiation 116 being provided, a second image is captured by the imaging component 104 in step S208. In embodiments comprising two or more imaging components, preferably a second imaging component captures the second image. Preferably the second image is captured in step S208 after any fluorescence caused by the excitation radiation 116 provided in step S202 has decayed away, such that there is no component due to fluorescence caused by excitation radiation 116 in the second image. Advantageously this makes the image subtraction process and any subsequent image processing as described below more accurate and less computationally complex. The time taken for the fluorescence to decay away will vary depending on the fluorescent material 123 used, but is typically in the range of 0.5 to 20 nanoseconds for photon emissions with energies from the UV to near infrared.

Optionally at step S210, the device 100 is configured to perform an image alignment algorithm as known in the art to align the first and second images. This allows for effective subtraction of the first and second images as described below, and is particularly advantageous in the event that the device 100 is handheld and or moving whilst the process is being performed—the optional alignment step S210 avoids the introduction of errors in the detection of the fluorescence introduced by the field of view of the imaging component 104 changing between taking the first and second images. In some embodiments, device 100 further comprises one or more sensors for detecting the position and/or motion of the device 100, wherein the alignment processing is based on information regarding the movement and/or change in position of the device 100 provided by the sensors.

In step S212 the second image is subtracted from the first image. The image subtraction is a process whereby the digital numeric value of a whole image is subtracted from another image on a point to point basis to detect the changes between the two images. The result of the image subtraction is a difference image. Since the first image was taken under background radiation 118 and excitation radiation 116, and the second image was taken under background radiation 118 only, the difference image substantially corresponds to an image of the fluorescence of the fluorescent material 123 only. Thus, the difference image can be used to identify any areas in which the fluorescent material 123 is present. Beneficially the present invention substantially removes contributions to the image due to background illumination 118, allowing the detection of fluorescence (and therefore surface defects in NDT processes for example) even in the presence of high background situations. Indeed, the present invention allows detection of fluorescent radiation of 200 lux or lower, when the fluorescent material is under background illumination of 100,000 lux or higher. Thus advantageously the present invention can be deployed in outdoor situations without the need to provide tents or awnings to lower ambient light levels, even in direct sunlight. Thus, the invention can provide a faster, most cost-effective mechanism for detecting fluorescence in an NDT setting. Similarly, the present invention can be deployed in indoor situations without the need to dim the ambient lighting, even when the ambient lighting is of high intensity. This is particularly advantageous in medical settings, such as operating theatres.

Optionally the method 200 also comprises step S214 in which additional image processing is performed. This additional processing preferably includes one or more of: digital signal processing (DSP)-assisted noise reduction, median filtering and contrast enhancements such as histogram equalisation. Advantageously, this helps to provide a clearer difference image in which any detected fluorescence can be more easily seen. It is noted that whilst step S214 is preferably performed on the difference image resulting from step S212, is further embodiments step S214 is performed before step S212, i.e. on the first and second images. In yet further embodiments the step S214 is performed before and after step S212.

In optional step S216, the resulting difference image (including the results of any additional processing performed in step S216) is displayed to a user. In such embodiments the difference image is preferably shown to the user in real-time thus allowing the user to visually identify an area in which the fluorescent material is present. Such an arrangement is advantageous in an NDT setting where the fluorescence corresponds to a crack or other surface defect on an item, thus allowing defects to be easily detected. Similarly, in a clinical setting the substantially real time identification of fluorescent agents that highlight cancers that need to be removed, or critical structures that must be avoided (such as bile ducts, ureters, nerves, and vessels), is advantageous as the surgeon can identify these in real time during the procedure. The difference image is preferably displayed either via a display on the device 100 itself (advantageously providing a self-contained unit), or alternatively via a display on an optional computing system 112.

Alternatively, or in addition, the difference image is analysed to automatically identify features corresponding to fluorescence from the fluorescent material 123. For example, the additional image processing of step S214 comprises performing automatic feature recognition. The automatic feature recognition is configured to identify regions in the difference image corresponding to contributions from the detected fluorescence. In response to identifying these regions, a user can be alerted to the presence of the defect (for example via a visual or audible alert produced by the device 100). In addition to using known feature recognition provisions, a preferred embodiment implements a machine learning algorithm. In particular, artificial neural networks are used to enable the system to train itself to automatically detect regions of interest, such as a fault or defect, that are distinguishable from the general background of the difference image. Advantageously, this allows the system to not only detect defects automatically, but to improve accuracy of automatic detection. This is particularly effective when the system 100 is being used in a manufacturing scenario to analyse similar components on a production line.

Steps S212 and optional steps S210 and S214 are preferably performed using imaging processing circuitry 106. In some embodiments the image processing circuitry is part of the device 100; alternatively the image processing circuitry is part of a computing device (such as the optional computing device 112). Thus, the image processing can be performed either: at the device 100 itself, advantageously enabling the device to provide a self-contained fluorescence detection unit, or; at a computing system, for example a pre-existing external computing system, thereby reducing the hardware required at the device, reducing the cost to manufacture the device as well as reducing the power consumed by the device.

In the preferred embodiment, the device 100 (or system as described above, or the system discussed below with reference to FIGS. 5A to 5B) is configured to repeat the method 200 to provide a temporal sequence of difference images. Beneficially this allows to a sequence of difference images to be created effectively in real-time, thus giving a user a real-time indication of which locations on a sample 114 correspond to accumulations of the fluorescent material 123. This is particularly useful when the position and/or orientation of the imaging component 104 is changed over time, for example when scanning over a large area of one or more samples 114 (e.g. when performing NDT inspection). Similarly, this is useful if the sample 114 itself is moving. In order to achieve this, the device 100 is preferably configured such that excitation source 102 flashes on and off and is synchronised with the frame rate of the imaging component 104. Preferably the rate at which the excitation source 102 flashes on and off is double the frame rate of the imaging component 104 ensuring first and second images (i.e. images with and without excitation radiation 116) can be captured as fast as the imaging component allows. Preferably synchronisation circuitry 108 controls the excitation source 102 and the imaging component 104 in order to achieve the above synchronisation. In embodiments comprising two or more imaging components, the frame rate is increased by cycling through the imaging components to capture each image as the method 200 is repeated, as discussed in more detail below.

The device 100 is optionally configured to average (for example using the image processing circuitry 106) all the first images and also all the second images in a certain time period (after aligning the images, if necessary) and perform the image subtraction on the resulting averaged images—in other words, all the images taken in a predetermined period corresponding to the excitation source 102 being on are averaged, and all the images taken in the same period corresponding to the excitation source 102 being off are averaged, and then the resulting averaged "on" and "off" images are subtracted to create a difference image. Beneficially this further enhances the visibility of fluorescence in the resulting difference image. Preferably the number of images captured before the averaging is performed can be specified by a user, for example via a graphical user interface displayed on a display included in the device 100 or connected to the device 100.

Figure 3A:
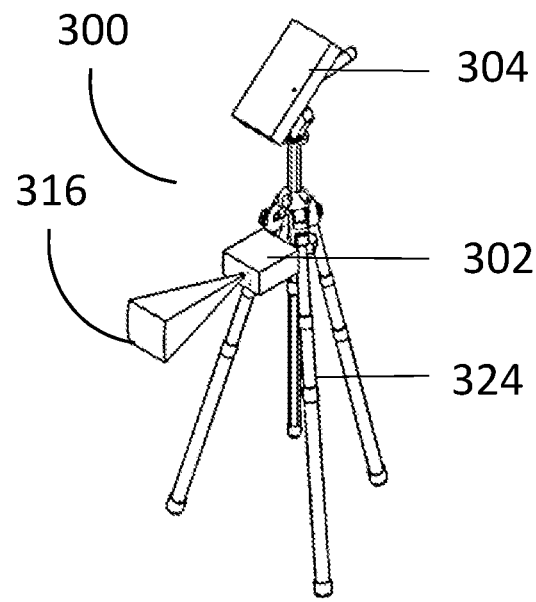
FIGS. 3A and 3B show a stationary system for detecting fluorescence signals in a first example of the present invention.
Figure 3B:
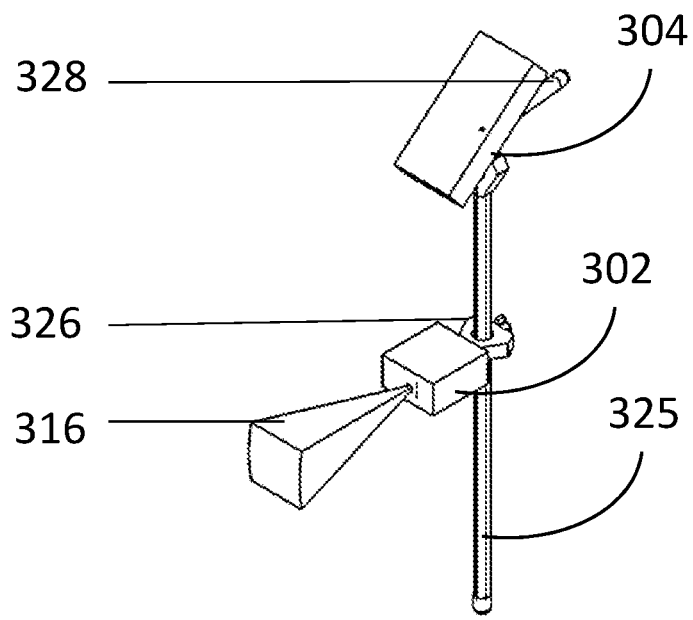

FIGS. 3A and 3B show a stationary system 300 for detecting fluorescence signals in a first example of the present invention. In this example there is provided an excitation source 302 such as the excitation source 102 described above, providing excitation radiation 316. There is also provided an imaging component 304 such as the imaging component 104 described above. In this example, the excitation source 302 and the imaging component 304 are provided as separate units, each attached to a mount 324. In this example mount 324 is shown as a tripod comprising a central support 325 to which the excitation source 302 and the imaging component 304 are attached, however other mounts suitable for supporting the various components of the system 300 will be appreciated by the person skilled in the art. In this example the excitation source 302 and the imaging component 304 each comprise an adjustment means 326, 328, configured to allow the positions and orientations of the excitation source 302 and the imaging component 304 to be independently adjusted. Such adjustment means 326, 328 preferably takes the form of a releasable bracket, a tripod head as typically used in photography, or any suitable means known to the skilled person. The system 300 preferably also comprises image processing circuitry and synchronisation circuitry (not shown) either in one or more units attached to the mount, or in an external computing system in communication with the imaging component 304 and the excitation source 302. Advantageously the example in FIGS. 3A and 3B allows for excitation radiation 316 to be provided along an axis different to that of the optical axis of the imaging component 304. This provides enhanced ability to adjust the excitation illumination according to the sample being observed. Additionally, as the system 300 is stationary during image capture and fluorescence detection, little or no image alignment processing is required, reducing the demand placed on processing resources in the system. This stationary example, with the appropriate optics, is particularly suited to assessing large areas of a sample with the ultimate limiting factor being the minimum number of pixels in the detector array required to distinguish a differentially imaged object or region of interest from the background noise floor, and can be easily set up at a desired location using the tripod arrangement.

Figure 4A:
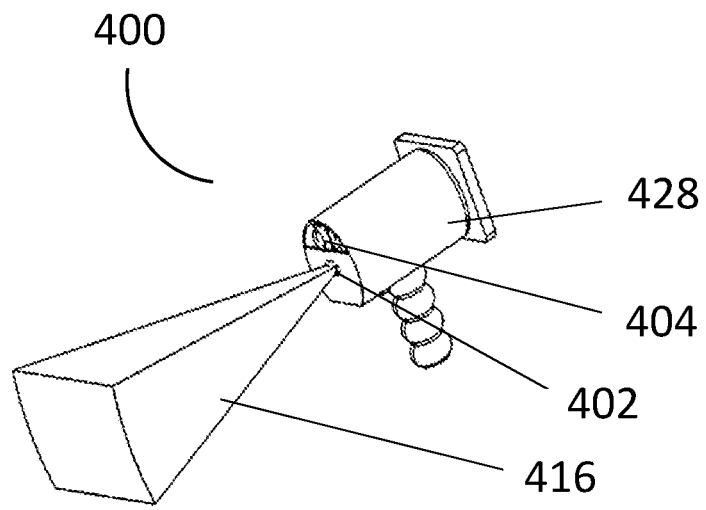
FIGS. 4A and 4B show a handheld device for detecting fluorescence signals in a second example of the present invention.
Figure 4B:
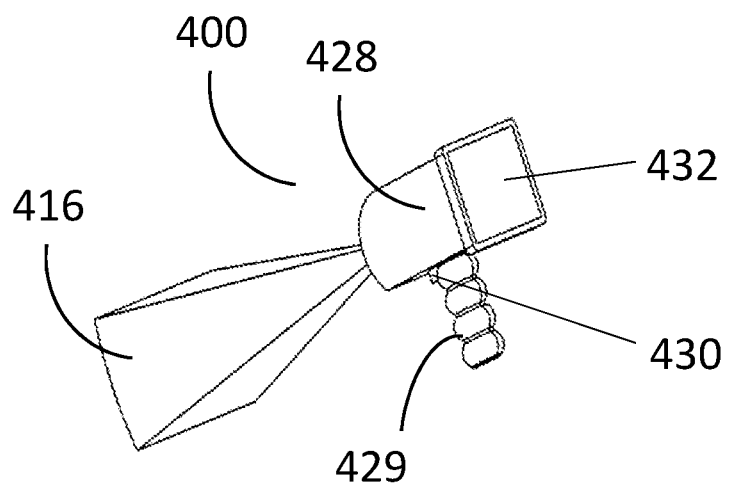

FIGS. 4A and 4B show a handheld device 400 for detecting fluorescence signals in a first example of the present invention. In this example there is provided an excitation source 402 such as the excitation source 102 described above, providing excitation radiation 416. There is also provided an imaging component 404 such as the imaging component 104 described above. In this example, the excitation source 402 and the imaging component 404 are provided within a housing 428, the housing 428 including one of more openings to allow excitation radiation 416 to leave the housing and to allow the imaging component 404 to capture images of an item of interest. In this example the handheld unit comprises a handle 429 and a push button 430. The device 400 is configured to start performing fluorescence detection in line with the method 200 discussed above when the push button 430 is actuated. Preferably the push button 430 is positioned on the handle 429 advantageously allowing the handheld device 400 to be operated with one hand. In this example the device 400 further comprises a display 432, wherein the device 400 is configured to display obtained difference images on the display 432, thereby giving a user a visual indication of whether the item(s) being observed have fluorescent material of interest present. In this example, preferably image processing circuitry and synchronisation circuitry (not shown) are housed within the housing 428. Preferably the housing also contains display circuitry (not shown) configured to cause the display 432 to display the difference images. Advantageously, as this device 400 is a self-contained and held unit, it is highly portable. This makes it convenient for transportation, convenient when moving position to scan around an object in three dimensions, and also for scanning objects in confined or otherwise difficult to access environments.

Figure 5A:
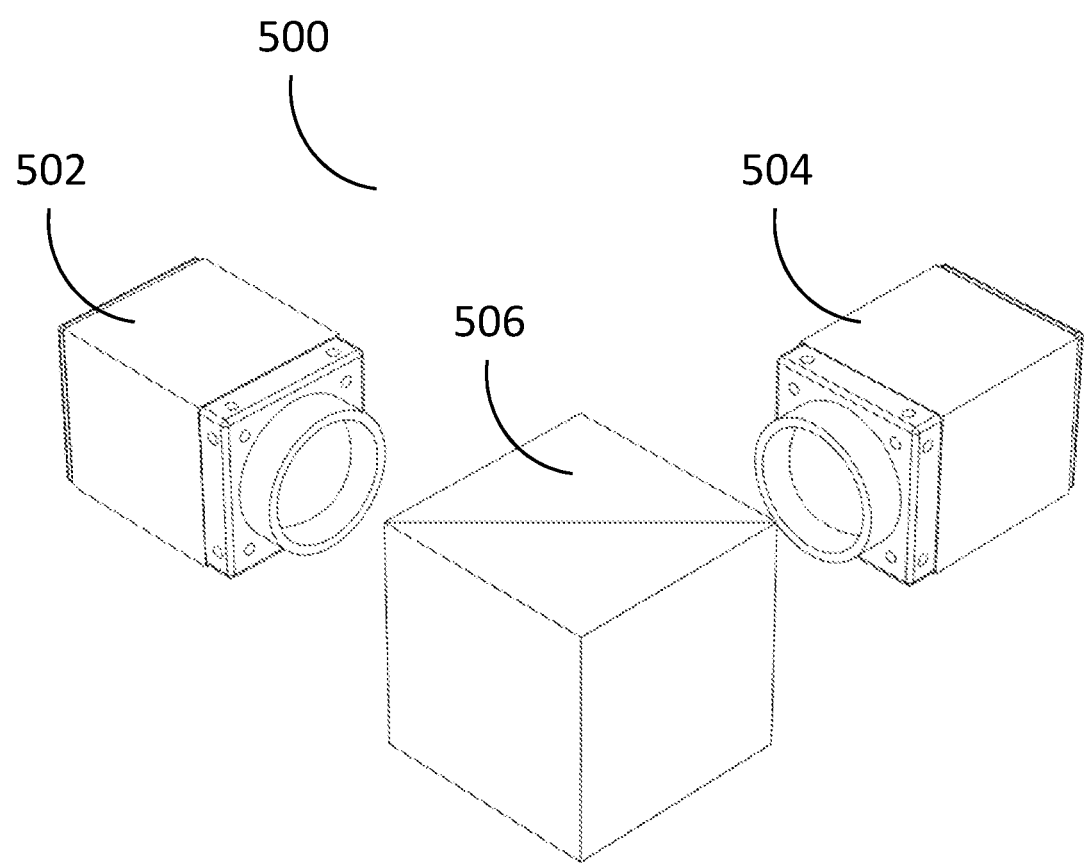
FIGS. 5A and 5B show schematics of a device comprising two synchronised imaging components and a beam splitter according to an aspect of the invention.
Figure 5B:
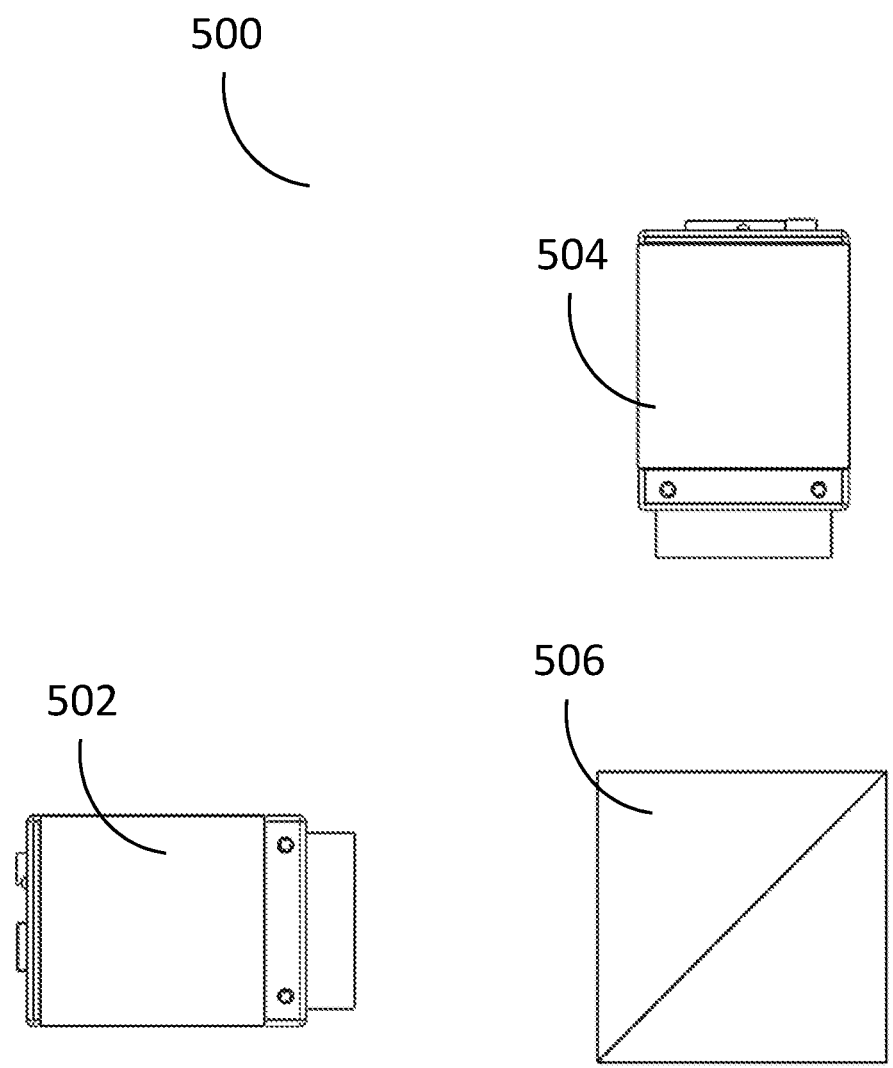

FIGS. 5A and 5B show a perspective view and a top-down view of an imaging device 500 in accordance with one embodiment of the invention respectively. The imaging device 500 comprises two imaging components 502, 504 and a beam splitter 506. The imaging components 502, 504 are preferably digital cameras (thus this embodiment provides a "dual-camera" arrangement). In this embodiment, the imaging device 500 is used in place of the single imaging component 104 in the system/device 100. In use the beam splitter 506 splits light incident on the imaging device 500 such that a portion of the incident light is directed onto one of the imaging components 502 and a portion is directed onto the other imaging component 504. Advantageously the two imaging components 502, 504 can be synchronised such that they each capture an image in turn, thereby effectively increasing the image capture frame rate of the device 100.

Figure 5C:
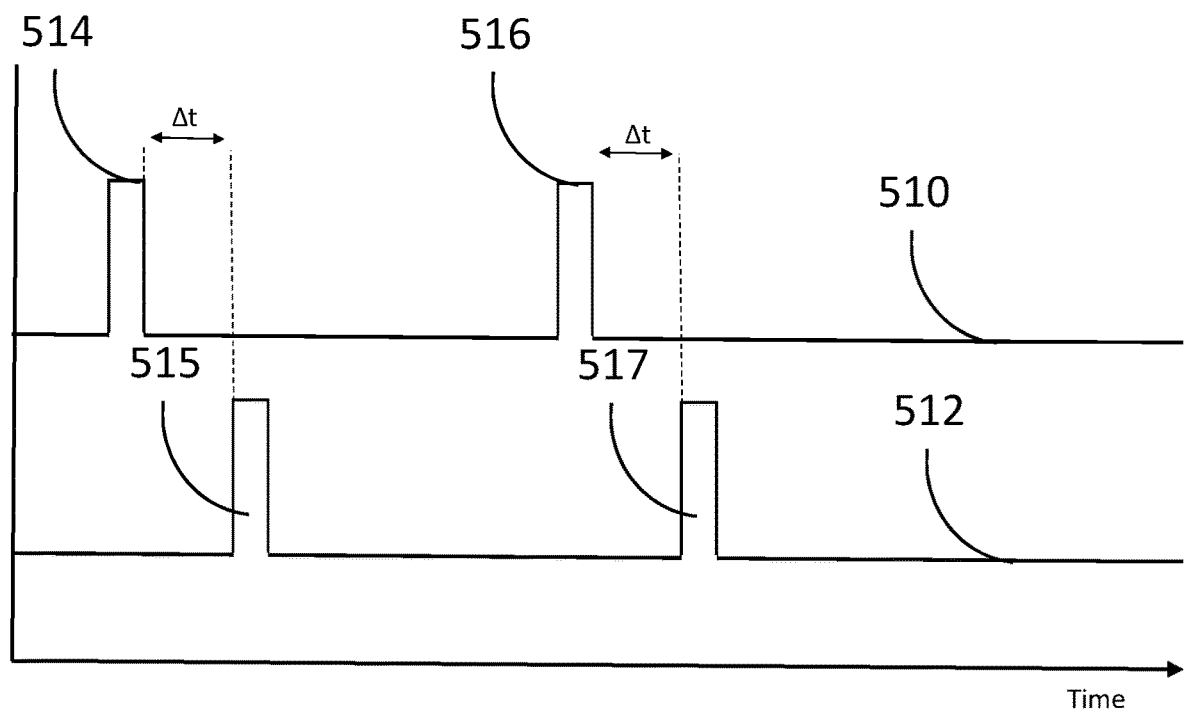
FIG. 5C illustrates continuously variable intervals between successive frames obtainable with a device comprising two synchronised imaging components according to an aspect of the invention.

FIG. 5C shows a first control signal 510, and a second control signal 512 configured to cause the first imaging component 502 and second imaging component 504 respectively to capture an image. The peaks 514, 515, 516, 517 correspond to the associated imaging component capturing an image. Images taken by the first imaging component 502 correspond to images taken under illumination by excitation radiation and images taken by the second imaging component 502 correspond to images taken in the absence of excitation radiation, or vice versa. The imaging components 502, 504 are preferably synchronised such that the time Δt between the first 502 and second imaging component 504 capturing an image (i.e. the interval between successive frames) is constant. The excitation source 102 is preferably synchronised with the increased image capture frame rate, thereby increasing the rate at which difference images can be obtained. Advantageously, this arrangement allows Δt to be continuously variable, and be orders of magnitude smaller than would otherwise be possible with a single camera alone, in turn allowing for a faster frame rate and thereby increasing the effectiveness of real-time detection of the fluorescent material. This "dual-camera" arrangement facilitates the taking of the two images required to produce a difference image in rapid succession, enabling clear detection of defects even if the device 500 or the object of interest is moving—in particular this mitigates undesirable motion effects resulting from the two images used in the difference image being taken at different times and device's view of the object of interest changing over time. Preferably Δt is of the order of a few microseconds, for example between 1 and 10 microseconds. Additionally, this permits a given area of the sample to be assessed in a shorter amount of time, as it takes less time to capture the images. Furthermore, this results the provision of more data for the purpose of further analysis of the fluorescence indicated. The embodiment of FIGS. 5A-5C is optionally provided in either the stationary system discussed above in relation to FIGS. 3A and 3B, or the handheld device as discussed in relation to FIGS. 4A and 4B. Whilst this embodiment is discussed above in relation to two imaging components, in further embodiments more than two imaging components are provided, preferably including a plurality of beam splitters—such further embodiments have benefits in further increasing the frame rate of the system/device 100.

Whilst FIGS. 5A-5C are discussed in relation to two imaging components 502, 504, it will be appreciated that further imaging components can be provided, and the device 500 cycles through each of the imaging components such that each imaging component takes an image in turn.

Although the above discussion is provided with reference to detecting fluorescence for fluorescent materials, it will be appreciated that all the embodiments above can be used to detect any form of stimulated emission from a material of interest, using a radiation source suitable for inducing stimulated emission in the material, and using the lock-in difference imaging techniques discussed above.

Furthermore, the above embodiments are also applicable for detecting absorption in a material of interest. In this case, the same systems, devices and methods can be used as discussed above, but rather than using an excitation source, a source of probe radiation is used, wherein the probe radiation is chosen so as to be preferentially absorbed by the material of interest. In this case, the first image corresponds to background radiation reflected from the sample, and additionally probe radiation reflected from areas of the sample in which the material of interest is not present. The second image corresponds to background radiation reflected from the sample. Thus, the difference image represents probe radiation reflected from areas of the sample not including the material of interest—the material of interest is identifiable from a lack of exposure (i.e. dark areas) in the difference image.

The above embodiments are provided by way of example only. Further aspects to the invention will be apparent from the appended claim set.

The invention claimed is:

1. A system for detecting a material of interest, comprising:
   a radiation source;
   a plurality of imaging components; and
   a display;
   wherein, in use, the system is configured to:
   a) emit probe radiation from the radiation source for a first time period, the radiation having a wavelength suitable for interacting with the material of interest;
   b) capture a first image via a first imaging component, the first image comprising a first component due to background illumination and a second component due to interaction of the probe radiation with the material of interest;
   c) stop emitting radiation for a second time period;
   d) capture a second image via a second imaging component, the second image substantially consisting of the first component;
   e) create a difference image corresponding to the difference between the first and second images, such that the difference image includes any features due to interaction of the probe radiation with the material of interest;
   wherein the system is further configured to display the difference image on the display;
   wherein the system is further configured to:
   repeat operations a) to e) so as to create a plurality of difference images; and
   display the plurality of difference images in real-time on the display.

2. The system of claim 1 wherein the system is further configured to cause each imaging component of the plurality of imaging components to capture an image in a temporal sequence.

3. The system of claim 1 wherein the probe radiation has a wavelength suitable for inducing stimulated emission in the material of interest, wherein the second component corresponds to stimulated emission from the material of interest.

4. The system of claim 1 wherein the probe radiation has a wavelength suitable for inducing fluorescence in the material of interest, wherein the second component corresponds to fluorescence from the material of interest.

5. The system of claim 1 wherein the probe radiation has a wavelength suitable for being absorbed by the material of interest, wherein the second component corresponds to reflection of the probe radiation by the material of interest.

6. The system of claim 1 wherein the system is further configured to capture the first image via the imaging component during the first time period and capture the second image via the imaging component during the second time period.

7. The system of claim 1 wherein the system is configured to cycle through each of the plurality of imaging components when capturing successive images.

8. The system of claim 1 further comprising a processor, where in the processor is configured to perform step e) and is optionally further configured to control the radiation source and the imaging component.

9. The system of claim 1 wherein the system is further configured to prevent the probe radiation contributing to the first image.

10. The system of claim 9 wherein the system further comprises one or more filters configured to substantially prevent radiation of wavelengths corresponding to the probe radiation from reaching the plurality of imaging components.

11. The system of claim 1 wherein the system is further configured to switch the radiation source on and off at a frequency that is double a frame rate of the plurality of imaging components.

12. The system of claim 1 further comprising a mount configured to support the radiation source, the imaging component and the processor.

13. The system of claim 12 wherein the mount is configured to be handheld.

14. The system of claim 1 further comprising a housing, wherein at least one of the radiation sources and the imaging component is included within the housing.

15. The system of claim 1 further comprising one or more filters configured to preferentially allow radiation of wavelengths corresponding to stimulated emission signals to reach the imaging component.

16. The system of claim 1 wherein the system is configured to act as a device for detecting a material of interest.

* * * * *